US00PP10533P

United States Patent [19]

Pouw

[11] Patent Number: Plant 10,533

[45] Date of Patent: Aug. 4, 1998

[54] HYBRID TEA ROSE PLANT NAMED 'RUIROUG'

[75] Inventor: A. A. Pouw, Pl De Kwakel, Netherlands

[73] Assignee: De Ruiter's Nieuwe Rozen B.V., Pl De Kwakel, Netherlands

[21] Appl. No.: 789,829

[22] Filed: Jan. 28, 1997

[51] Int. Cl.[6] ..... A01H 5/00

[52] U.S. Cl. ..... Plt./20

[58] Field of Search ..... Plt./11, 20, 16, Plt./17

*Primary Examiner*—Howard J. Locker
*Attorney, Agent, or Firm*—Christie, Parker & Hale, LLP

[57] ABSTRACT

A new variety of hybrid tea rose plant producing bright red flowers suitable for growing under glass.

1 Drawing Sheet

BACKGROUND OF THE INVENTION

The present invention relates to a new and distant variety of rose plant of the hybrid tea rose class which was created by crossing undistributed, unnamed and unpatented seedlings as seed and pollen parents in De Kwakel, Holland. The varietal denomination of the new variety is 'Ruiroug'. The new variety was isolated and asexually reproduced by budding in De Kwakel, Holland.

SUMMARY OF THE INVENTION

Among the novel characteristics possessed by this new variety which distinguish it from its parents and all other varieties of which I am aware are its attractive bright red flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in De Kwakel, Holland shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (RHSCC) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.
Class: Hybrid Tea.

As can be seen in the accompanying detail illustration there is shown a new shoot and green bud, 1; compound three, five and seven leaflet leaves, 2, 3 and 4, respectively;

a stem, 5; bud, 6; a flower, 7, about one-third open; a flower, 8, about one-half open; and a flower, 9, more fully open. Also shown are flower stems 10, 11 and 12, with reproductive organs displayed.

The following further horticultural description is based on observations made of specimens grown under glass in De Kwakel, Holland.

Flower

Blooming habit: Nearly continuous.

A. Bud:

(1) *Size.*—Medium, about 3 to 4 cm long and about 3 cm wide.

(2) *Form.*—Broad ovate (shape of longitudinal section just before separation of sepals); urn-shaped after sepals part.

(3) *Color.*—As sepals divide, near 42A to 44A, 44B.

(4) *Sepals.*—Much longer than green bud, very foliated, upperside near 138B, underside near 137C.

(5) *Peduncle.*—Long: Strength-erect, very strong. Color—near 147B, few hairs or prickles, about 17 cm.

B. Bloom:

*Flower.*—Medium; viewed from above—irregularly rounded; viewed from side—(a) upper part of fully opened flower, flattened convex; (b) lower part of fully opened flower, flat.

(1) *Size.*—Average size when fully expanded—about 9 cm.

(2) *Borne.*—Singly, one to a stem.

(3) *Form.*—Decorative type, somewhat flat top, spiral imbricated, petals ruffled at margin.

(4) *Petalage.*—Fully double, about 25, about 5 petaloids, about 2×2 cm, crinkled.

(5) *Color.*—After sepals part and petals unfurl, near 42A to 44B; flower color near 42B to 44B; petal undersurface near 45A. Zone of petal attachment near 4B to 4C. Overall tonality from a distance is attractive bright red.

(6) *Peduncle.*—Generally smooth.

(7) *Fragrance.*—Weak.

(8) *Length of stem*.*—About 85 cm.

(9) *Production*.*—About 165/m$^2$/yr.

*Average, actual depends on circumstances of cultivation.

Petals:

(1) *Texture.*—Crisp.

(2) *Appearance.*—Inside velvety and outside satiny.

(3) *Form and size.*—Broad, medium to strong undulation of margin.

(4) *Arrangement.*—Regularly arranged, imbricated.
(5) *Petaloids.*—Several, about 5.
(6) *Lasting quality.*—Long-lasting quality on plant and after cutting; Vase life is about 15 days. Blooms on plant last for about 20 days. When temperature is low, sometimes there is difficulty in flower opening.

Reproductive Organs

A. Stamens, filaments and anthers:
*Arrangement and color.*—Regularly arranged around styles; color of filaments—pink.
B. Pollen:
*Color.*—Yellow.
C. Styles: Long, stigma above mouth of receptacle, pale yellow.
D. Stigmas: Yellow, positioned below anthers.
E. Hip: Funnel-shaped; small seed vessel at petal fall but very few seeds set.

Plant

A. Form: Narrow bushy, average disease resistance.
B. Growth: Vigorous, about 2 m in height, about 0.6 m in width.
C. Foliage: Compound 3, 5 and 7 leaflets.
(1) *Size.*—Medium width and length, about 14 to 16 cm in length.
(2) *Quantity.*—Abundant.
(3) *Color.*—Juvenile foliage—bronze to reddish brown; near 183A; weak to medium anthocyanin coloration, (shoot about 20 cm long); mature leaf color—near 147A, upperside near 137A, underside near 137C.
(4) *Shape.*—Broad oval.
(5) *Texture.*—Upper side is medium glossy; underside is matte.
(6) *Edge.*—Serrate.
(7) *Serration.*—Ordinary, acuminate apices.
(8) *Leaf stem.*—Color—near 147A to 147B.
(9) *Stipules.*—Short, simple, medium green, distinct auricle.
(10) *Leaflets.*—Cross section—slight concave: medium undulation of margin; terminal leaflet—long and broad; blade about 6 to 7 cm long and 4 to 5 cm wide, rounded base.
D. Wood:
(1) *New wood.*—Color—near 146 B to 146 C; young shoots have weak to medium anthocyanin; coloration—bronze red purple to reddish brown.
(2) *Old wood.*—Color—near 147B to 147C.
E. Prickles (thorns):
(1) *Prickles.*—Present; quantity (main stalk)—ordinary; shape of lower side—concave; Length—short prickles few, long prickles, medium; Color—near 180B; Position—irregular.
F. Disease resistance: Average resistance to powdery and downey mildew.

What is claimed is:

1. A new and distinct rose plant of the hybrid tea rose class, substantially as shown and described.

* * * * *

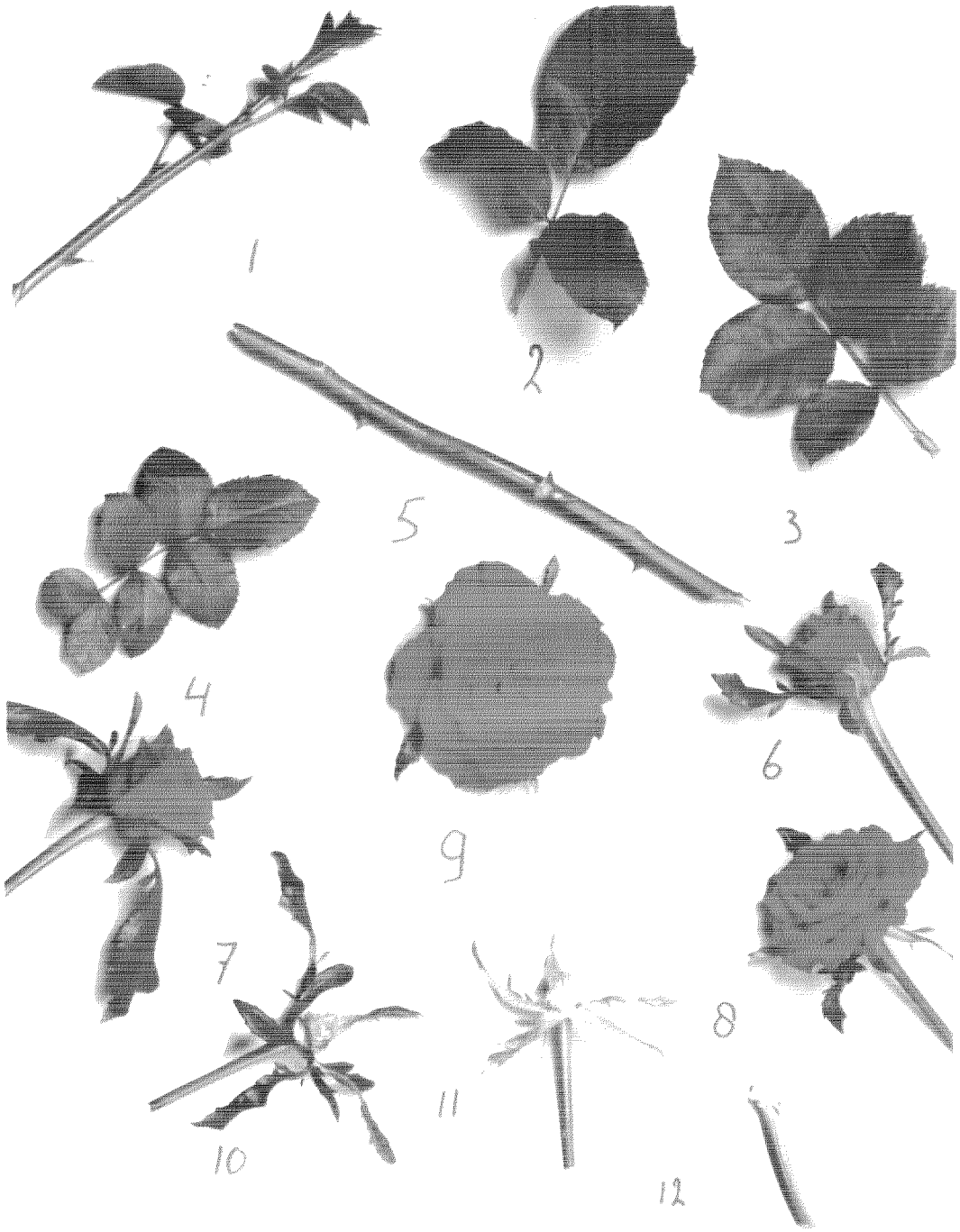
1
2
3
4
5
6
7
8
9
10
11
12